(12) United States Patent
Zukowski

(10) Patent No.: US 11,752,302 B1
(45) Date of Patent: Sep. 12, 2023

(54) INDWELLING VALVE ACTUATED URINARY CATHETER

(71) Applicant: Stanislaw Zukowski, Flagstaff, AZ (US)

(72) Inventor: Stanislaw Zukowski, Flagstaff, AZ (US)

( * ) Notice: Subject to any disclaimer, the term of this patent is extended or adjusted under 35 U.S.C. 154(b) by 0 days.

(21) Appl. No.: 18/070,421

(22) Filed: Nov. 28, 2022

(51) Int. Cl.
*A61M 25/00* (2006.01)

(52) U.S. Cl.
CPC .... *A61M 25/0075* (2013.01); *A61M 25/0017* (2013.01); *A61M 2025/0018* (2013.01); *A61M 2025/0076* (2013.01); *A61M 2202/0496* (2013.01); *A61M 2210/1085* (2013.01); *A61M 2210/1096* (2013.01)

(58) Field of Classification Search
CPC .......... A61M 25/0075; A61M 25/0017; A61M 2025/0018; A61M 2025/0076; A61M 2202/0496; A61M 2210/1085; A61M 2210/1096; A61M 25/04; A61M 2210/1089; A61M 25/0074; A61M 2025/0004; A61M 2025/0079; A61M 2025/0175; A61M 39/22; A61M 2039/226
See application file for complete search history.

(56) References Cited

U.S. PATENT DOCUMENTS

| | | | | |
|---|---|---|---|---|
| 396,754 | A * | 1/1889 | Mayfield | A61M 39/26 604/249 |
| 2,156,522 | A * | 5/1939 | Bowmer | A61M 27/00 417/511 |
| 3,438,366 | A * | 4/1969 | Smith | A61B 10/0291 600/570 |
| 3,841,308 | A * | 10/1974 | Tate | A61M 25/0075 604/528 |
| 4,194,513 | A * | 3/1980 | Rhine | A61B 10/0291 600/563 |
| 4,432,757 | A | 2/1984 | Davis, Jr. | |
| 4,932,938 | A | 6/1990 | Goldberg et al. | |
| 4,946,449 | A | 8/1990 | Davis, Jr. | |
| 5,041,092 | A | 8/1991 | Barwick | |
| 5,112,306 | A * | 5/1992 | Burton | A61F 2/0027 604/101.02 |
| 5,707,357 | A | 1/1998 | Mikhail et al. | |
| 6,050,934 | A | 4/2000 | Mikhail et al. | |
| 6,217,549 | B1 * | 4/2001 | Selmon | A61M 29/02 604/105 |

(Continued)

*Primary Examiner* — Adam Marcetich
(74) *Attorney, Agent, or Firm* — Invention To Patent Services; Alex Hobson

(57) ABSTRACT

An indwelling valve actuated urinary catheter has an inner catheter having an inlet port configured on a distal end and for locating within the bladder and a sheath that extends over the inner catheter to produce a valve. The sheath extends over the inlet port when the valve is in a closed position and manipulation of a valve actuator on the proximal end, located within the penis, opens the valve. A bladder plug configured on the distal end of the inner catheter may form a seal between the catheter sheath and the inner catheter. The valve actuator may comprise a proximal nodule and a distal nodule that are configured within the urethra along the penis. Manual manipulation of the valve actuator through the penis, such as by pinching the penis, moves the proximal and distal nodules with respect to each other to open or close the valve.

6 Claims, 6 Drawing Sheets

(56) References Cited

U.S. PATENT DOCUMENTS

| | | | |
|---|---|---|---|
| 8,096,986 B2 | 1/2012 | Armistead | |
| 8,475,435 B2 | 7/2013 | Bolmsjo et al. | |
| 8,633,268 B2 | 1/2014 | Lawson et al. | |
| 9,173,753 B1 | 5/2015 | Zukowski | |
| 10,010,392 B1 | 7/2018 | Zukowski | |
| 2003/0208183 A1* | 11/2003 | Whalen | A61M 25/0017 604/544 |
| 2005/0038413 A1* | 2/2005 | Sansoucy | A61M 25/0075 604/537 |
| 2006/0111691 A1* | 5/2006 | Bolmsjo | A61M 25/0017 604/544 |
| 2006/0167438 A1 | 7/2006 | Kalser et al. | |
| 2006/0205997 A1 | 9/2006 | Whalen | |
| 2006/0287570 A1 | 12/2006 | Whalen | |
| 2007/0078389 A1 | 4/2007 | Whalen | |
| 2007/0232981 A1* | 10/2007 | Ravenscroft | A61M 25/0075 604/6.16 |
| 2008/0114286 A1 | 5/2008 | Hamel et al. | |
| 2008/0287888 A1* | 11/2008 | Ravenscroft | A61M 25/0068 604/249 |
| 2010/0312225 A1* | 12/2010 | Armistead | A61M 25/0075 606/108 |
| 2012/0004645 A1 | 1/2012 | Dastani | |
| 2013/0289527 A1* | 10/2013 | Ravenscroft | A61M 25/0075 604/508 |
| 2022/0362514 A1* | 11/2022 | Xiang | A61M 25/0017 |

\* cited by examiner

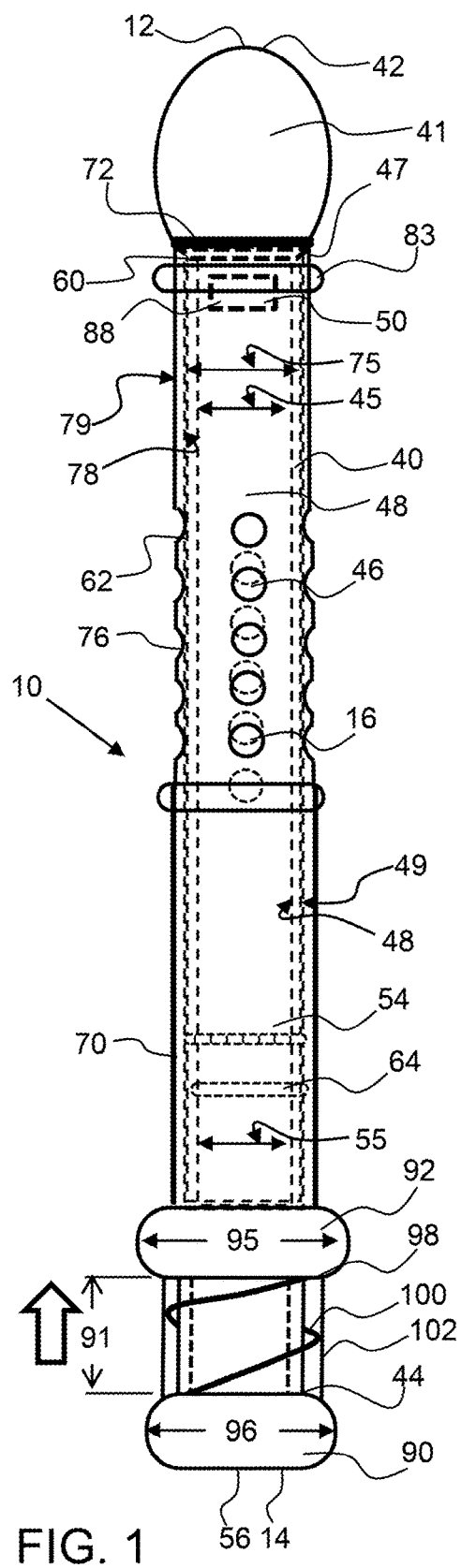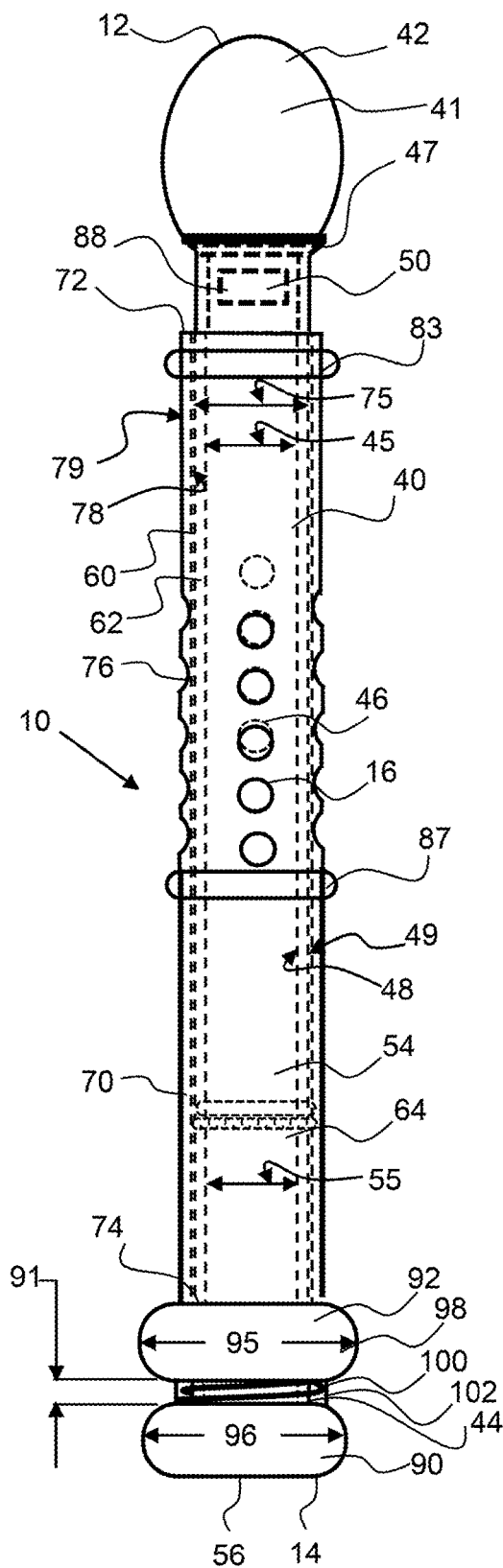
FIG. 1
FIG. 2

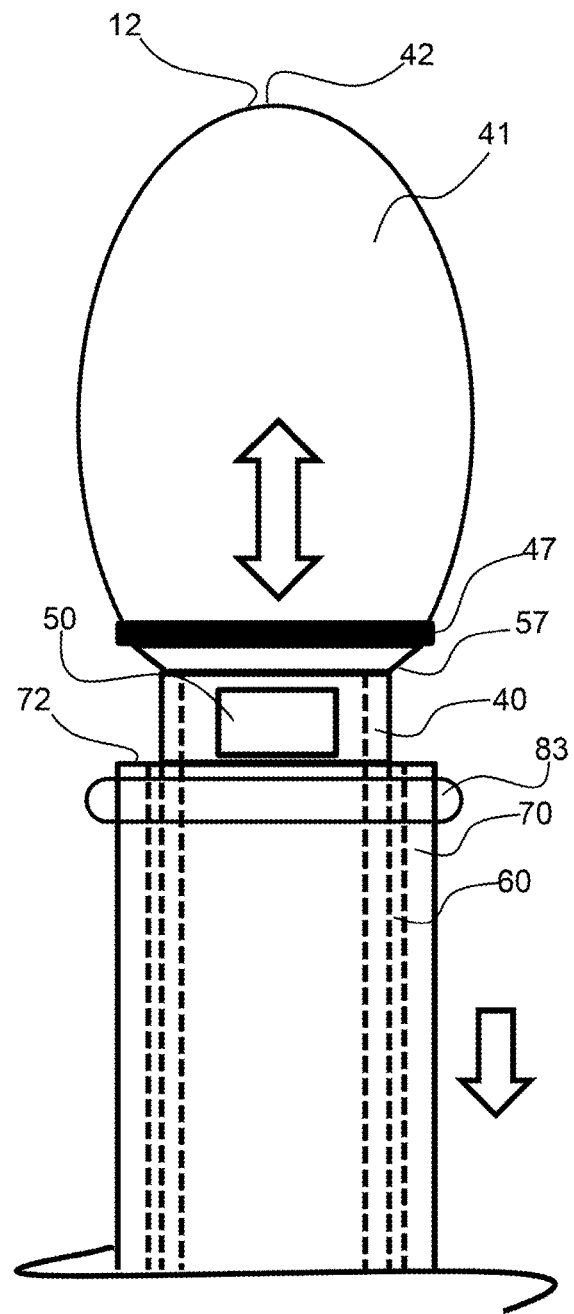
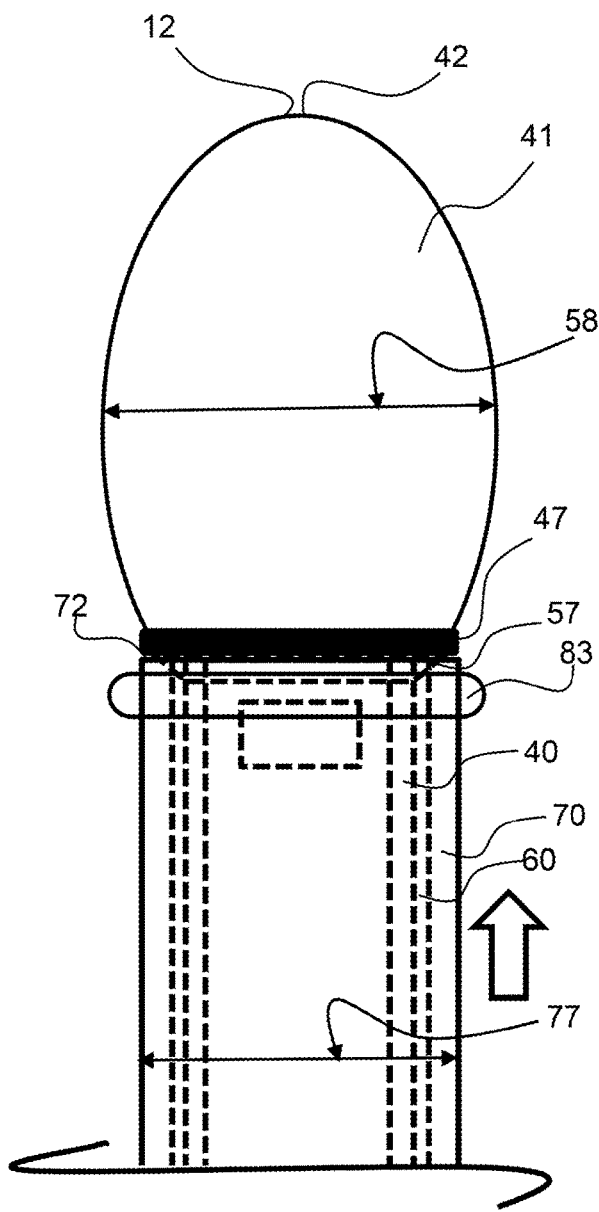
FIG. 5
FIG. 6

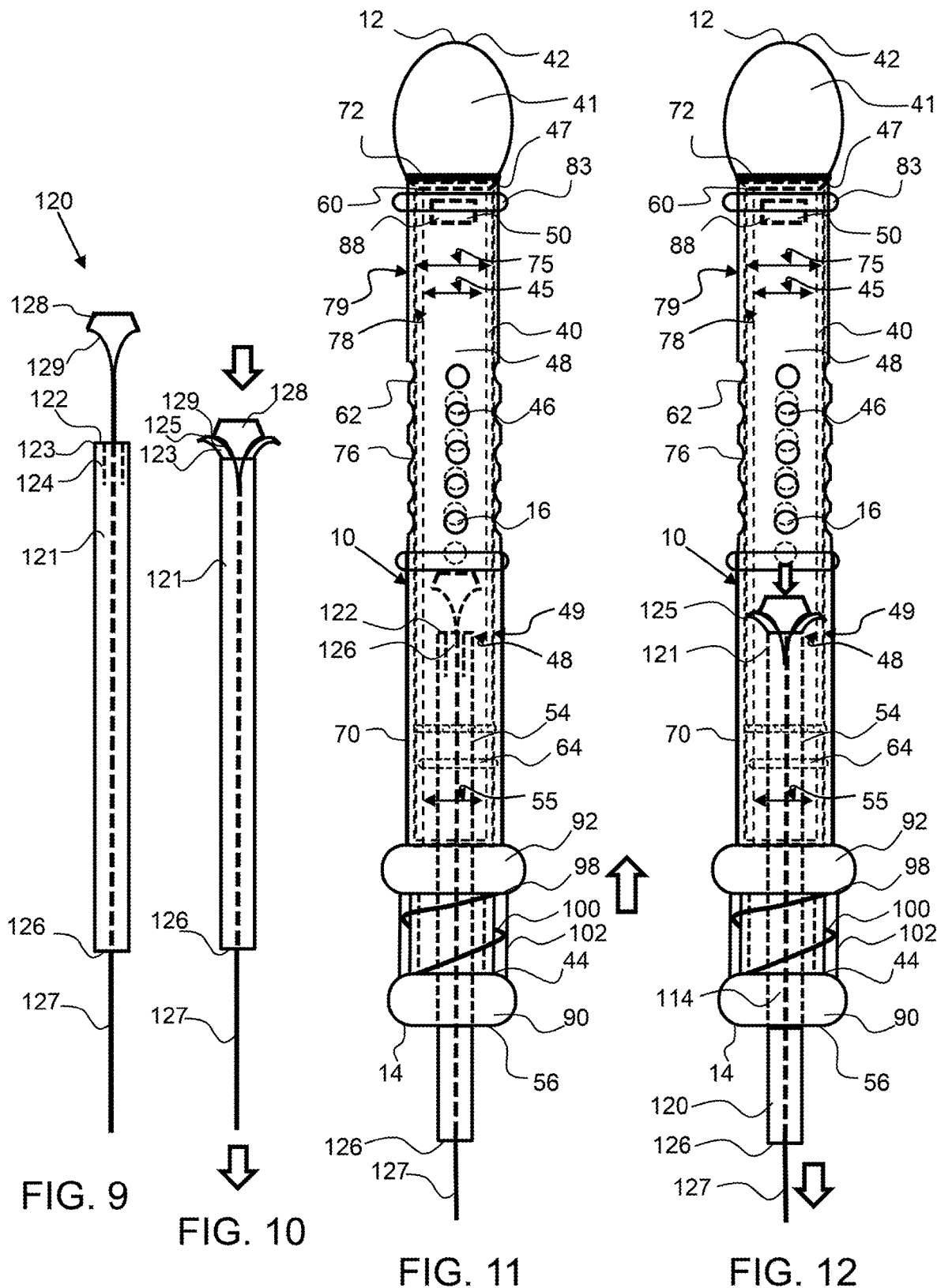

INDWELLING VALVE ACTUATED URINARY CATHETER

BACKGROUND OF THE INVENTION

Field of the Invention

The invention is directed to indwelling catheters having a valve on the distal end of the catheter that extends into the bladder that is manipulated by a valve actuator located within the penis.

Background

Catheters are routinely inserted through the urethra and extend into the bladder to expel urine. Indwelling catheters typically have a portion that extends out of the penis that can be manipulated to allow urine to be expelled. In some cases, a valve is configured on the outer extended portion of the catheter. Manipulation of the outer extended portion is cumbersome and prevents a person from participating in intercourse. Some indwelling catheters are configured within the urethra and do not extend out from the penis but require insertion of an instrument to initiate the flow of urine. This is cumbersome and embarrassing for the user as they have to carry instruments with them to restroom. These indwelling catheters also retain urine as the valve is configured on the proximal end, or end closest to the tip of the penis and the full catheter is prone to leaking as it is full of urine at all times.

SUMMARY OF THE INVENTION

The invention is directed to an indwelling valve actuated urinary catheter that comprises an inner catheter having an inlet port configured on a distal end and for locating within the bladder, and a sheath that extends over the inner catheter to cover the inlet port and produce a valve. The sheath may extend over the inlet port when the valve is in a closed position and the inner catheter may be manipulated by a valve actuator on the proximal end, and located within the penis, to move the inner catheter with respect to the sheath to open the valve. The inner catheter may be moved forward into the bladder by the valve actuator to move the distal end of the inner catheter out from the distal end of the sheath to expose the inlet port and open the valve to allow urine to flow from the bladder into the inner catheter. The inner catheter may be moved within the sheath or moved with respect to the sheath to expose the inlet port within the bladder. The valve actuator may comprise a proximal nodule and a distal nodule that are configured within the urethra along the penis. Manual manipulation of the valve actuator through the penis, such as by pinching the penis, moves the proximal and distal nodules with respect to each other to open or close the valve. The proximal nodule of the valve actuator may be moved toward the distal nodule to move the inner catheter out from the distal end of the sheath.

An exemplary indwelling valve actuated urinary catheter allows a user to open and close the valve by simple manual manipulation of the valve actuator within the penis. The exemplary indwelling valve actuated urinary catheter will remain empty of urine as the valve is sealed by being located within the sheath. The inlet port may be configured proximal the bladder until the inner catheter is moved forward into the bladder to expose the inlet port. A bladder plug may be configured on distal end of the inner catheter and configured to produce a seal against the distal end of the sheath. The spring in the valve actuator may pull the inner catheter into the sheath to effectively seal the bladder plug against the distal end of the sheath. In addition, an exemplary indwelling valve actuated urinary catheter may comprise a retaining feature that keeps the valve open so that the user can expel urine from their bladder without holding the valve open. The retaining feature may be a recess and protrusion configured in the interface surfaces of the outside surface of the inner catheter and the inside surface of the sheath. The protrusion may be configured to seat within the recess to retain the indwelling valve actuated catheter open within holding the proximal nodule of the valve actuator.

The indwelling valve actuated urinary catheter is configured for insertion into the urethra to locate the distal end of the inner catheter and bladder plug in the bladder. A sheath distal prostate prominence and sheath proximal prostate prominence may be configured to retain the indwelling valve actuated urinary catheter in position, wherein the prominences are located next to the internal urethral sphincter and external urethral sphincter, respectively. These prominences may be toroid in shape, or rings around the sheath, for example. A sheath distal prostate prominence may extend from the distal end of the sheath and may be configured to be located distal the internal urethral sphincter and may be located within the bladder. The location of the sheath distal prostate prominence may prevent the sheath from being pulled proximal toward the penis or out of the bladder. This may keep the bladder plug within the bladder. A sheath proximal prostate prominence may be configured to be located proximal an external urethral sphincter to prevent the sheath from being pushed distal and out of position. The positioning of these two prominences may keep the sheath from being moved proximal or distal out of position.

An exemplary valve actuator comprises a proximal and distal nodule that are moved with respect to each other to change an offset distance between them to open and close the valve. The sheath may be attached to the distal nodule and movement of the inner catheter by movement of the distal nodule toward the proximal nodule may open the valve from a closed position. The inner catheter may be attached to the proximal nodule and movement of the inner catheter by movement of the proximal nodule toward the distal nodule may open the valve from a closed position. The proximal nodule may be moved toward the distal nodule to push the inner catheter out from the distal end of the sheath to expose the inlet port within the bladder to allow urine to flow into the inner catheter. A spring element may be configured between the proximal and distal nodules and may provide an extension force to keep an expanded offset distance between the nodules to keep the valve closed. The spring may pull on the inner catheter to pull a bladder plug, configured on the distal end of the inner catheter, toward and against the distal end of the sheath. A user may have to overcome the force of the spring element to move the proximal and distal nodule with respect to each other to open the valve. A spring cover may extend over the spring, such as a spring cover tube, to prevent the spring from being exposed to the inside surface of the urethra, to prevent any pinching.

An exemplary indwelling valve actuated urinary catheter may comprise a retaining feature that keeps the valve open to allow a user to continue to expel urine or urinate without holding the nodules at a required offset distance. An exemplary retaining feature comprise a protrusion and/or detent in the inner surface of the sheath and outer surface of the inner catheter, or the interface, that creates an interference to maintain an offset distance. For example, a sheath may comprise toroid shaped or ring-shaped protrusion along the inner surface that seats into a ring-shaped detent around the outer surface of the inner catheter. In another embodiment, the sheath comprises a ring-shaped protrusion on the inside surface and the inner catheter comprises a ring shaped protrusion from the outer surface and these two protrusion are force past each other when the proximal and distal nodules are moved to open the valve to create an interference that keeps the valve open. The interference force of the retainer feature, or force required to move the sheath and inner conduit with respect to each other to dislodge the retainer feature may be greater than the spring element force.

An exemplary indwelling valve actuated urinary catheter may also comprise one or more prostate apertures to allow the prostate to expel secretions through the catheter. A sheath prostate aperture may be aligned with an inner prostate aperture, or prostate aperture in the inner catheter while the valve is in a closed position and/or when in an open position. In an exemplary embodiment, a plurality of prostate apertures may be partially aligned while in the closed and/or open position.

An exemplary indwelling valve actuated urinary catheter comprises a sheath having a distal end that is more distal than the inlet port when in closed position. The proximal nodule of the valve actuator may be moved closer to the distal nodule to move the distal end of the inner catheter out from the distal end of the sheath. The spring element provides an extension force to keep the distal end of the inner catheter and the bladder plug pulled against the distal end of the sheath to keep the inlet port and the valve closed when not in use.

An exemplary indwelling valve actuated urinary catheter may be provided in a size to fit a person's anatomy. The length may be 10 cm or more, 20 cm or more, 30 cm or more, 40 cm or more, and any range between and including the length values provided. The diameter of an exemplary indwelling valve actuated urinary catheter may be 10 French (Fr) or more, 20Fr or more, about 40Fr or more, about 50Fr or less and any range between and including the French sizes provided.

A method of urinating utilizing an exemplary indwelling valve actuated urinary catheter comprises the steps of inserting the exemplary indwelling valve actuated urinary catheter through the urethra and locating the valve in the bladder and locating the valve actuator along the penis. To help with insertion or removal of the indwelling valve actuated urinary catheter, a special tool or a small size balloon catheter may be used. A balloon catheter may be inserted into the inner catheter of the indwelling valve actuated urinary catheter and expanded to retain the balloon against the inside surface of the inner catheter. The catheter portion of the balloon catheter may then be used to push the indwelling valve actuated urinary catheter into the urethra of the penis and into position. As described herein the sheath distal prostate prominence may be configured distal the internal urethral sphincter and the sheath proximal prostate prominence may be configured proximal the external urethral sphincter. A user may then manipulate the valve actuator by moving the proximal nodule of the valve actuator toward the distal nodule to move the inner catheter with respect to the fixed sheath. The sheath is retained in position by the sheath distal and proximal prostate prominences. Movement of the inner catheter exposes the inlet port within the bladder to allow urine to flow into the inner catheter and out of the penis to expel urine from the bladder. A user may release the valve actuator and a spring element may return the proximal nodule to a closed position, or a position wherein the valve is closed.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 1 shows an exemplary indwelling valve actuated urinary catheter having a valve in a closed position configured on the distal end of the catheter and a valve actuator configured on the proximal end.

FIG. 2 shows an exemplary indwelling valve actuated urinary catheter having a valve in an open position configured on the distal end of the catheter and a valve actuator configured on the proximal end.

FIG. 5 shows the distal end of the valve actuated urinary catheter with the inner catheter actuated out and away from the distal end of the sheath to expose the inlet port and open the valve.

FIG. 6 shows the distal end of the valve actuated urinary catheter with the inner catheter retracted back against the distal end of the sheath, wherein the plug seal seals the bladder plug to the distal end of the sheath.

FIG. 9 shows an exemplary retrieval implement having a retrieval portion with flanges that are expanded out radially by the expander portion when the expander portion is pulled into the retrieval portion.

FIG. 10 shows the expander portion of the retrieval implement being pulled into the retrieval portion with the flanges flared outward along the flared surfaces of the expander portion.

FIG. 11 shows the retrieval implement inserted into the inner conduit of the exemplary indwelling valve actuated urinary catheter.

FIG. 12 shows the expander portion of the retrieval implement being pulled into the retrieval portion and the flanges of the retrieval portion being flared outward along the flared surfaces of the expander portion to press the flange tips against the inside surface of the inner catheter, for retrieval.

Figure 3:
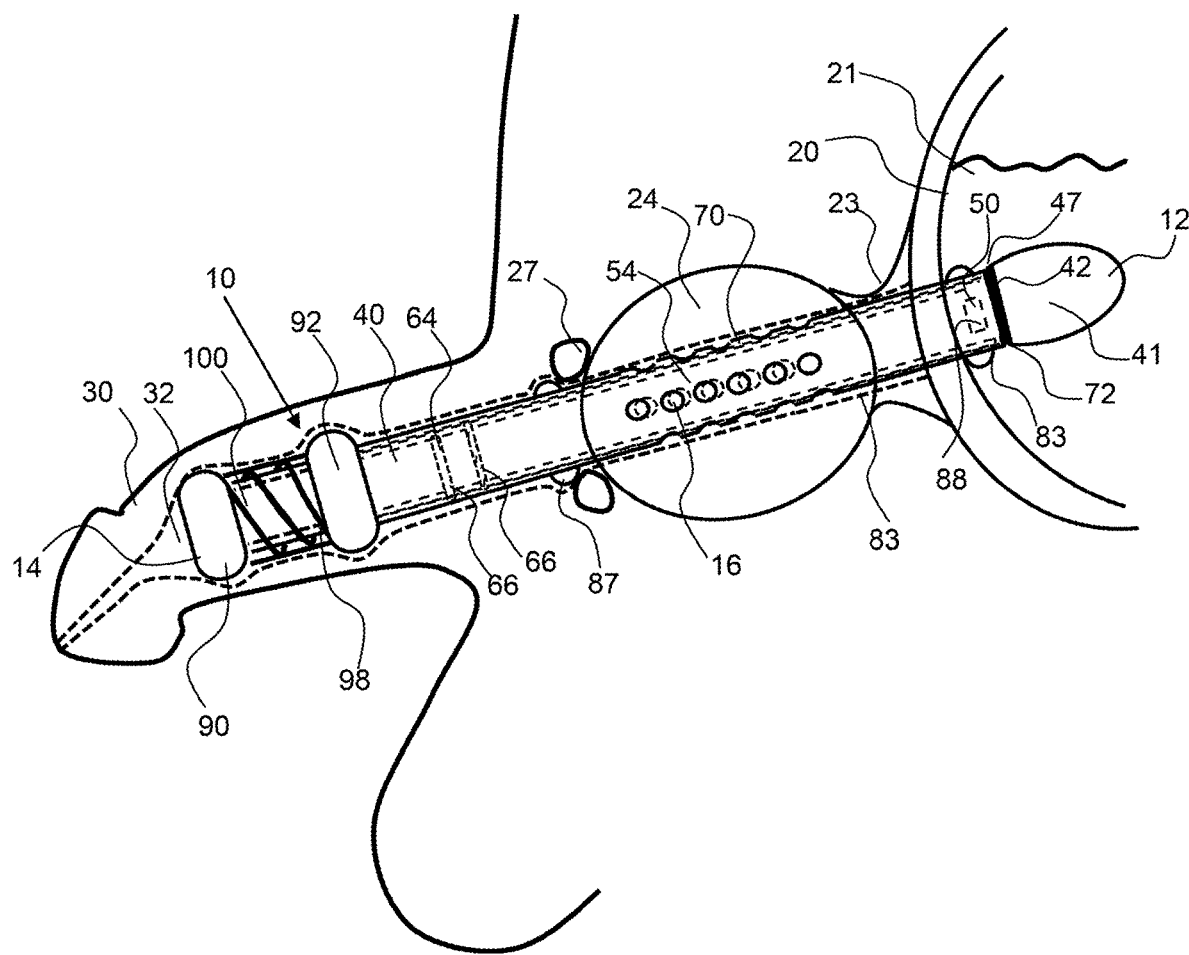
FIG. 3 shows an exemplary indwelling valve actuated urinary catheter inserted into a urethra with the distal end and valve configured within the bladder and the valve actuator configured within the penis.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

Referring to FIGS. 1 and 2, indwelling valve actuated urinary catheter 10 has a valve 88, or inlet port 50 on the distal end 12 of the catheter and a valve actuator 98 configured on the proximal end 14 of the catheter. The valve comprises an inlet port 50 configured through the inner catheter 40. As shown in FIG. 1, the valve 88 is in a closed position with the inlet port 50 configured within the sheath and with the bladder plug 41 sealed to the distal end 72 of the sheath 70 by the plug seal 47, which includes a tapered plug portion that extends into the distal end of the sheath. As shown in FIG. 2, the valve 88 is in an open position with the inlet port 50 exposed to allow fluid, such as urine from the bladder to flow into the inner conduit of 54 of the catheter that has an inner conduit diameter 55. The inner conduit allows urine to pass from the valve 88 to the conduit outlet 56.

The valve is actuated by a valve actuator 98 configured on the proximal end of the catheter. The valve actuator comprises a proximal nodule 90 and a distal nodule 92 coupled together by a spring element 100. A spring cover 102 extends around the spring to prevent any pinching of tissue by the spring. The catheter sheath 70 is coupled with the distal nodule 92 and when the offset distance 91 between the proximal and distal nodule is reduced, as shown in FIG. 2, the inner catheter is pushed out from the distal end 72 of the sheath 70 to expose the inlet port 50. The proximal nodule 90 is actuated toward the distal nodule 92 to compress the spring element 100. The spring element 100 may return the inner catheter 40, by moving the inner catheter with respect to the sheath. This spring pulls the bladder plug 41 toward and against the distal end of the sheath to close the valve 88 after urine has been expelled through the catheter and penis. The proximal nodule 90 has a diameter 96 and the distal nodule 92 has a diameter 95, and these diameters may be different, wherein the distal nodule may be bigger in dimension or have a larger diameter than the proximal nodule. These different diameters may aid in locating and moving the proximal nodule with respect to the distal nodule.

The inner catheter 40 has a length from a distal end 42 to the proximal 44. The inner catheter 40 is coupled with the proximal nodule 90, but not with the distal nodule 92. The inner catheter has an inner catheter diameter 45 an inside surface 48 and an outside surface 49. The catheter sheath 70 has a length from a distal end 72 to the proximal end 74. The catheter sheath 70 is coupled with the distal nodule 92, but not with the proximal nodule 90. The catheter sheath has an inner diameter 75 an inside surface 78 and an outside surface 79. The catheter sheath extends around the inner catheter and slides along the length axis when the valve actuator is manipulated. A lubricant 62, such as a hydrogel may be configured in the interface 60 between the inner catheter 40 and the catheter sheath 70.

A plurality of prostate apertures 16 are configured in an exemplary indwelling valve actuated urinary catheter 10 to allow prostate secretions from the prostate 24 to pass into the inner conduit 54 of the catheter. The catheter sheath 70 has prostate apertures 76 and the inner catheter 40 has prostate apertures 46, and these apertures may be at least partially aligned when the valve is in a closed and/or open position.

A retainer feature 64 may keep the valve in an open position after it is manually opened and may comprise an enlarged outside surface feature of the inner catheter and a retainer ring on the inside surface of the catheter sheath 70. An interference between these two features in the interface 60 may require a force to push the retainer ring over the enlarged outside surface feature. After the retainer ring as passed over the enlarged outside surface feature of the inner catheter, the valve may stay open. The spring element may be selected to have a retraction force that is not sufficient to pull the retainer ring over the enlarged outside surface feature of the inner catheter. A person may have to manually move the distal nodule 92 to move the retainer ring over the enlarged outside surface feature, to close the valve.

The indwelling valve actuated urinary catheter 10 may be inserted into the urethra and located with the distal end and bladder plug in the bladder. A sheath distal prostate prominence 83 and sheath proximal prostate prominence 87 may be configured to retain the indwelling valve actuated urinary catheter 10 in position, wherein the prominences are located next to the internal urethral sphincter and external urethral sphincter, respectively.

As shown in FIG. 3, an exemplary indwelling valve actuated urinary catheter 10 is inserted into a urethra 32 with the distal end 12 and valve 88 and inlet port 50 configured within the bladder 20 and the valve actuator 98 configured within the penis 30. The sheath distal prostate prominence 83 and sheath proximal prostate prominence are configured next to the internal urethral sphincter 23 and external urethral sphincter 27, respectively, to retain the indwelling valve actuated urinary catheter 10, and more specifically the sheath 70, in position with respect to the bladder and prostate. The sheath distal prostate prominence 83 and sheath proximal prostate prominence 87 may be configured to retain the indwelling valve actuated urinary catheter in position, wherein the prominences are located next to the internal urethral sphincter 23 and external urethral sphincter 27, respectively. These prominences may be toroid in shape, or rings around the sheath, for example. A sheath distal prostate prominence may extend from the distal end of the sheath and may be configured to be located distal the internal urethral sphincter and may be located within the bladder. The location of the sheath distal prostate prominence 83 may prevent the sheath from being pulled proximal toward the penis or out of the bladder 20. This may keep the bladder plug 41 within the bladder. A sheath proximal prostate prominence 87 may be configured to be located proximal an external urethral sphincter 27 to prevent the sheath from being pushed distal and out of position. The positioning of these two prominences may keep the sheath from being moved proximal or distal out of position. The proximal and distal prostrate prominences of the sheath, retain the sheath in position to allow the inner catheter 40 to be moved with respect to the fixed position of the sheath.

As shown in FIG. 3, the valve is in a closed position and urine 21 within the bladder is not leaking into the inner conduit of the catheter. The spring element pushes on the sheath to keep the distal end 72 of the sheath 70 pushed against the bladder plug 41. The plug seal 47 is configured on the distal end 42 of the inner catheter 40 to retain a seal against the distal end of the sheath. The second nodule 92 is forced toward the distal end 12 by the spring element 100 and this keeps the distal end 72 of the sheath 40 configured over the inlet port 50, thereby sealing the valve 88 closed. The catheter remains void of urine until the catheter valve 88 is opened by actuating the proximal nodule 90 toward the distal nodule 92 to push the bladder plug 41 away from the distal end 72 of the sheath 70. The spring element 100 is compressed to open the valve 88.

Figure 4:
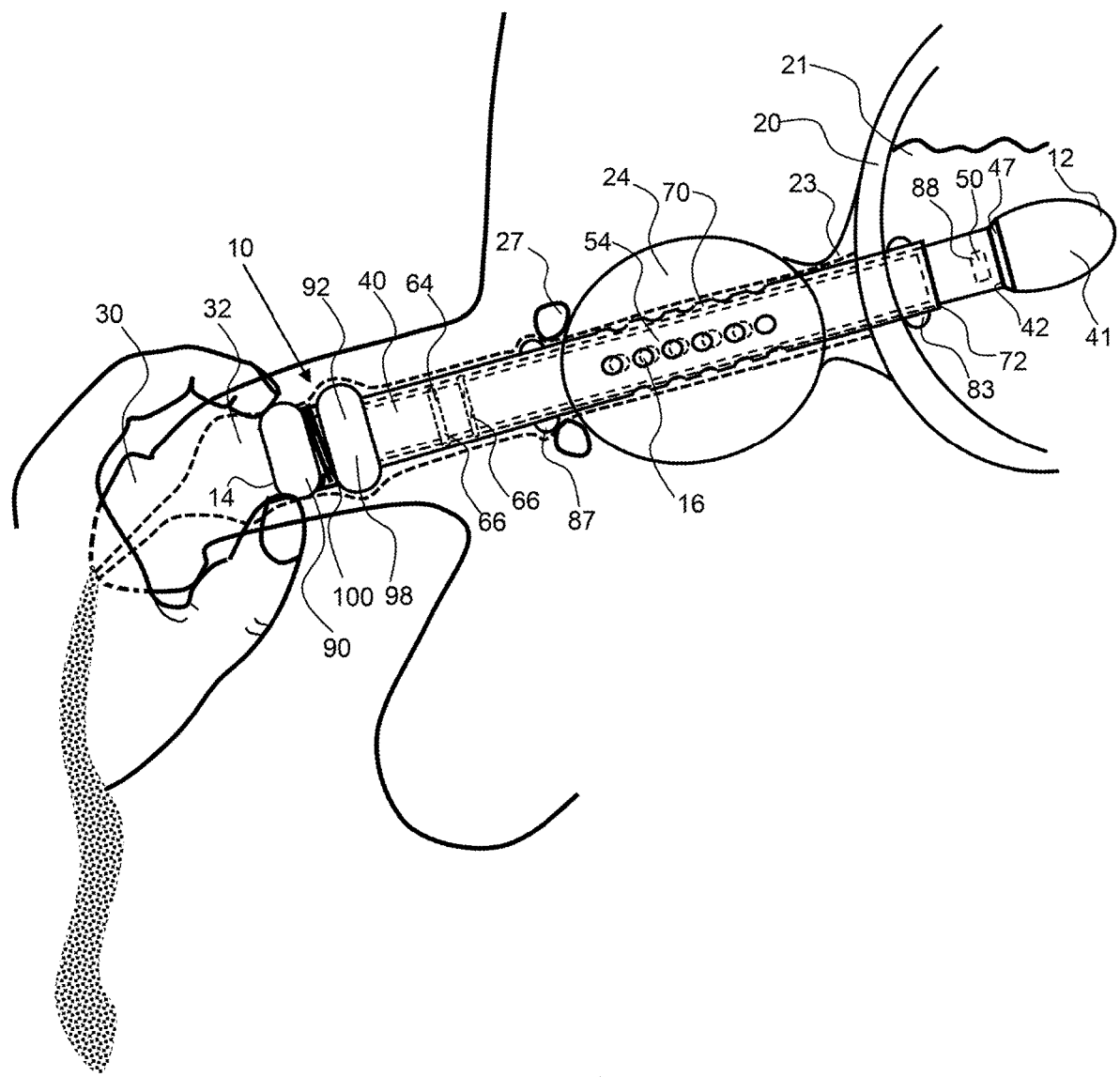
FIG. 4 shows an exemplary indwelling valve actuated urinary catheter inserted into a urethra with the distal end and valve configured within the bladder and the valve actuator configured within the penis and the valve being opened by a person's hand.

As shown in FIG. 4, an exemplary indwelling valve actuated urinary catheter 10 is inserted into a urethra 32 with the distal end 12 and valve 88 configured within the bladder 20 and the valve actuator 98 configured within the penis 30. The valve 88 is being manually opened by the person. The proximal nodule 90 is being pushed closer toward to the distal nodule 92 by the person's finger 37 and thumb 38. Moving the proximal nodule toward the distal nodule moves the inner catheter 40 within the fixed position sheath 70 to expose the inlet port 50 and allow urine 21 to pass from the bladder 20 into the inner conduit 54. The person is opening the valve in situ. Urine 21' and prostate secretions 25 are being expelled from the penis. Note that prostrate secretions may move into the inner conduit 54 with the valve in a closed position.

Referring now to FIG. 5, the distal end 12 of the valve actuated urinary catheter 10 and bladder plug 41 is configured with the inner catheter 40 actuated out from the distal end 72 of the sheath to expose the inlet port 50 in the inner catheter 40. A plug seal 47 is configured to seal the bladder plug over the distal end of the sheath 70 and may include a resilient material such as an elastomer that can be compressed to form a liquid seal, like an O-ring around the inner catheter 40. The plug seal 47 may have a tapered plug portion 57 that tapers from the bladder plug 41 toward the proximal end 14 and may be configured for insertion into the distal end 72 of the sheath 70. This tapering along geometry may provide an effective seal. The plug seal extends as a ring around the proximal end of the bladder plug.

As shown in FIG. 6, the distal end 12 of the inner catheter 40 is pulled back against the distal end 72 of the sheath 70. The spring pulls the bladder plug 41 back against the distal end of the sheath to create a seal and close the valve 88. The plug seal 47 seals the bladder plug to the distal end of the sheath 72. Note that a portion of the tapered plug portion 57 is configured within the sheath 70, or within the interface 60 between the sheath and the inner catheter 40. The diameter 58 of the bladder plug 41 may be greater than the outer diameter 77 of the sheath 70. As shown, the bladder plug tapers in diameter forming a tapered portion that is configured to extend, at least partially, into the catheter sheath to produce a seal and prevent fluid penetration through the distal end of the indwelling valve actuated urinary catheter 10 between the catheter sheath and the inner catheter.

Figure 7:
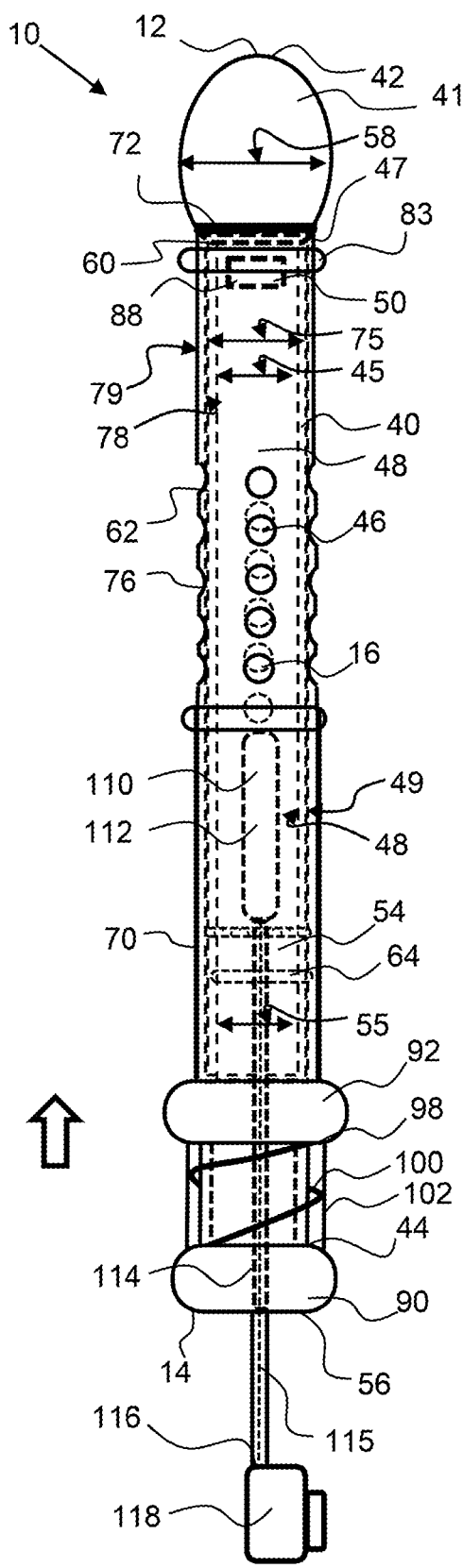
FIG. 7 shows an exemplary indwelling valve actuated urinary catheter having a balloon catheter inserted into the inner conduit with the balloon in the inner conduit and a catheter extending from the balloon to a proximal end.
Figure 8:
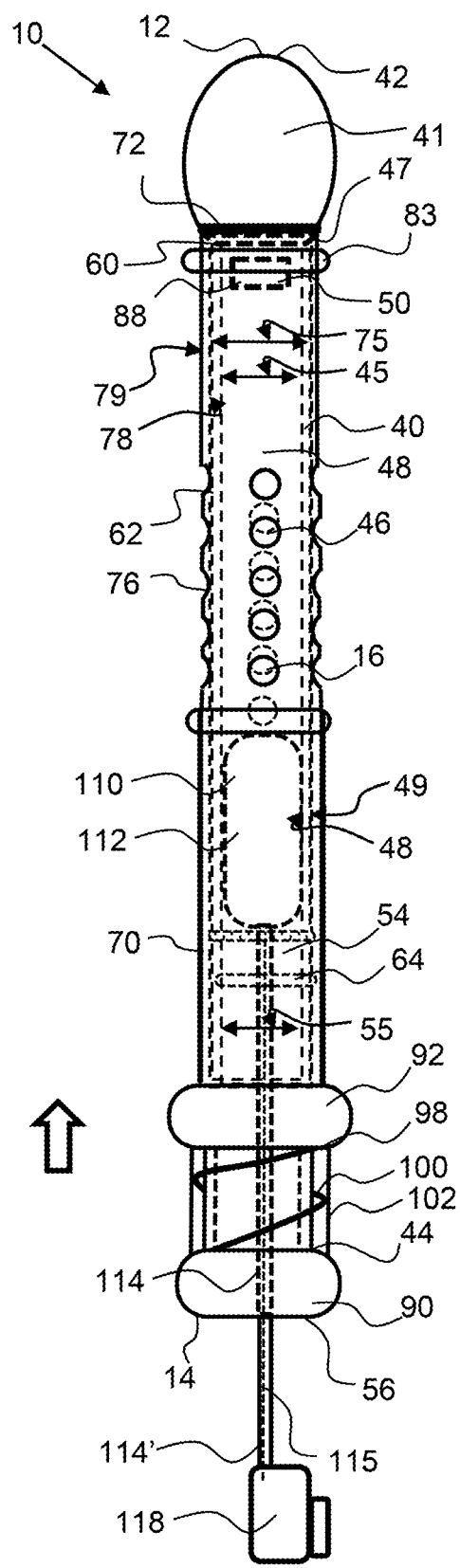
FIG. 8 shows the exemplary indwelling valve actuated urinary catheter shown in FIG. 6, with the balloon inflated via the inflation device to enable the indwelling valve actuated urinary catheter to be inserted into the urethra with the bladder plug and distal end within the bladder.

Referring now to FIGS. 7 and 8, an exemplary indwelling valve actuated urinary catheter 10 may be inserted into the urethra by utilizing a balloon catheter 110 inserted into the inner conduit 54 with the balloon 112 in the inner conduit and a catheter 114 extending from the balloon to a proximal end 116 configured outside of the body for inflation by the inflation device 118. As shown in FIG. 7, the balloon is not inflated and as shown in FIG. 8, the balloon is inflated. The balloon may be coupled to a guide wire 115 and be configured within the catheter for insertion and then the catheter may be pulled back to expose the balloon from the distal end of the catheter.

Referring now to FIGS. 9 to 11, an exemplary retrieval implement 120 has a retrieval portion 121 with flanges 123 that are expanded out radially by the expander portion 128 when the expander portion is pulled into the retrieval portion.

As shown in FIG. 9, the expander portion 128 is configured distal the distal end 122 of the retrieval portion 121. The expander portion 128 is coupled to a retrieval line 127 that extends through the retrieval portion 121 and the proximal end 126 of the retrieval portion 121. The retrieval portion may be a tube and the flanges may be formed by slits in the distal end of the tube. The retrieval portion has flanges that extend to an opening for receiving the expander portion 128. The expander portion has flared surfaces 29, that flare away from the distal end 122 of the retrieval portion 121. As shown in FIG. 10, the expander portion is pulled down into the retrieval portion and the flared surfaces 129 are causing the flanges 123, which may be formed by slits 124 in the distal end of a retrieval portion, to flare out radially to flange tips 125.

Referring now to FIGS. 11 and 12, the retrieval implement 120 is inserted into the inner conduit 54 of the inner catheter 40. As shown in FIG. 11, the expander portion 128 is configured distal the distal end 122 of the retrieval portion 121. As shown in FIG. 12, the expander portion 128 of the retrieval implement 120 is being pulled into the retrieval portion and the flanges 123 are flared outward along the flared surfaces 129 of the expander portion 128. The flange tips 125 are extending into the inside surface 48 of the inner catheter 40.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A valve actuated urinary catheter system comprising an indwelling valve actuated urinary catheter comprising:
   a) a length from a proximal end to a distal end of the indwelling valve actuated urinary catheter;
   b) an inner catheter comprising:
      i) a distal end;
      ii) a proximal end; and
      iii) a length from said distal end to said proximal end of the inner catheter;
      iv) an inner conduit;
   c) a catheter sheath having a length from a distal end to a proximal end of said catheter sheath;
      wherein the catheter sheath extends around the inner catheter;
   d) a valve configured on a distal end of said indwelling valve actuated urinary catheter; the valve comprising:
      i) an inlet port through the inner catheter for a flow of urine to pass into the inner conduit of the inner catheter;
   wherein the catheter sheath extends over the inlet port while the indwelling valve actuated urinary catheter is in a closed position;
   wherein the inlet port is configured to reside in a bladder during use of the indwelling valve actuated urinary catheter to drain urine from said bladder;
   e) a valve actuator configured on a proximal end of said indwelling valve actuated urinary catheter, said valve actuator comprising:
      i) a proximal nodule attached to the inner catheter;
      ii) a distal nodule attached to the catheter sheath;
      iii) a spring element that provides an extension force to increase the offset distance between the proximal and distal nodules;
      iv) a spring cover configured to extend around the spring element to prevent contact of the spring element with the urethra;
   wherein the spring cover extends from the proximal nodule to the distal nodule;
   wherein an offset distance between the proximal and distal nodules is changed manually by moving the proximal nodule with respect to the distal nodule to move the inner catheter to expose the inlet port to allow urine to pass into the inner conduit of the inner catheter, through the inner conduit and out of a penis; and
   wherein the valve actuator is configured to reside in said penis during use of the indwelling valve actuated urinary catheter to drain urine from said bladder;
   wherein the distal end of the catheter sheath is configured more distal than the inlet port while in a closed position to seal the inlet port by the catheter sheath;
   wherein the catheter sheath extends over the inlet port to seal the valve while in said closed position; and
   f) a bladder plug configured on the distal end of the inner catheter and comprising a plug seal configured to produce a seal between the bladder plug and the catheter sheath, while in said closed position;
   wherein the inner catheter is moved by decreasing the offset distance between the proximal and distal nodules to move the distal end of the inner catheter away from the distal end of the catheter sheath to expose the inlet port and open the valve to allow urine to pass into the inner conduit of the inner catheter and be expelled through the penis;
   wherein the bladder plug comprises a plug seal comprising a resilient material configured to form a seal between the bladder plug and the catheter sheath; and
   wherein the bladder plug comprises a tapered plug portion configured to extend into the catheter sheath;
   g) a retaining feature configured to retain the inner catheter in an offset position while the proximal nodule is actuated with respect to the distal nodule to change the offset distance;
   h) a sheath distal prostate prominence extending from an outside surface of the catheter sheath and configured to prevent the catheter sheath from being pulled proximally when the valve actuator is manipulated;
   wherein the sheath distal prostate prominence is configured to be positioned distal an internal urethral sphincter with the indwelling valve actuated urinary catheter inserted into the urethra with the bladder plug configured in the bladder;
   i) a sheath proximal prostate prominence extending from said outside surface of the catheter sheath and configured to prevent the catheter sheath from being pushed distally when the valve actuator is manipulated;
   wherein the sheath proximal prostate prominence is configured to be positioned proximal an external urethral sphincter with the indwelling valve actuated urinary catheter inserted into the urethra and the bladder plug configured in the bladder;
   j) a retrieval implement comprising a retrieval portion having flanges and an expander portion having flared surfaces and coupled to a retrieval line that extends through the retrieval portion, whereby pulling the retrieval line to actuate the expander portion into the retrieval portion causes the flanges to be deflected and flared radially outward to press against an inside surface of the inner catheter for retrieval.

2. The indwelling valve actuated urinary catheter system of claim 1, wherein the plug seal comprises silicone.

3. The indwelling valve actuated urinary catheter system of claim 1, wherein the tapered plug portion comprises said resilient material.

4. The indwelling valve actuated urinary catheter system of claim 1, wherein the sheath proximal prostate prominence and the sheath distal prostate prominence are toroid shaped and have an outer diameter that is greater than an outer diameter of the catheter sheath.

5. The indwelling valve actuated urinary catheter system of claim 1, wherein the spring element comprises a spring that coils around the inner catheter.

6. The indwelling valve actuated urinary catheter system of claim 1, wherein the inner catheter comprises an inner prostate aperture that extends through the inner catheter to allow passage of prostate secretions into the inner conduit; and wherein the sheath comprises a sheath prostate aperture that is aligned with the inner prostate aperture for the passage of prostate secretions into the inner conduit.

* * * * *